(12) United States Patent
Paz Briz et al.

(10) Patent No.: US 7,887,862 B2
(45) Date of Patent: Feb. 15, 2011

(54) METHOD AND APPARATUS FOR SEPARATING, PURIFYING, PROMOTING INTERACTION AND IMPROVING COMBUSTION

(75) Inventors: Fernando Roberto Paz Briz, Sinaloa (MX); Fernando Roberto Paz Alcazar, Margen Izquerdo Quevedo (EC)

(73) Assignee: Industrias Centli S.A. de C.V., Nuevo Leon (MX)

( * ) Notice: Subject to any disclaimer, the term of this patent is extended or adjusted under 35 U.S.C. 154(b) by 679 days.

(21) Appl. No.: 11/973,692

(22) Filed: Oct. 10, 2007

(65) Prior Publication Data

US 2009/0098266 A1  Apr. 16, 2009

(51) Int. Cl.
*A23L 1/025* (2006.01)

(52) U.S. Cl. .......... 426/18; 426/238; 426/618; 426/629; 426/634; 426/637; 426/483; 426/485; 426/518; 209/199; 209/200; 494/37; 241/9; 241/24.16; 241/24.26

(58) Field of Classification Search .......... 426/18, 426/237, 238, 478–479, 481–483, 518, 618, 426/629, 634, 637, 485; 209/199–200; 494/37; 241/24.1, 24.16, 24.26, 9

See application file for complete search history.

(56) References Cited

U.S. PATENT DOCUMENTS

| | | | |
|---|---|---|---|
| 2,752,097 A | 6/1956 | Lecher | |
| 3,244,361 A | 4/1966 | Lundahl | |
| 3,503,803 A | 3/1970 | Bennett et al. | |
| 3,533,567 A * | 10/1970 | Willems | 241/163 |
| 4,211,744 A | 7/1980 | Boucher | |
| 4,619,406 A | 10/1986 | Fishgal | |
| 4,802,897 A | 2/1989 | Johnson | |
| 4,938,622 A | 7/1990 | Stoerzbach | |
| 4,989,988 A | 2/1991 | Hütter et al. | |
| D320,851 S | 10/1991 | Störzbach | |
| 5,203,515 A | 4/1993 | Stoerzbach | |
| 5,358,725 A * | 10/1994 | Izumitani et al. | 426/238 |

(Continued)

FOREIGN PATENT DOCUMENTS

GB  702811  1/1954

(Continued)

OTHER PUBLICATIONS

Kinematica AG, Megatron System MT 5000, pp. 1-6, Dec. 2002, Switzerland.

(Continued)

*Primary Examiner*—Drew E Becker
(74) *Attorney, Agent, or Firm*—Stinson Morrison Hecker LLP

(57) ABSTRACT

An apparatus and method for separating joined components, purifying liquid, promoting interaction between two or more components and improving combustion. The apparatus has a housing, a rotor inside of the housing, a plurality of protrusions extending from the rotor, a shaft coupled with the rotor and a prime mover for rotating the shaft. Fluid within the housing cavitates as the rotor rotates and the protrusions move through the fluid. Cavitation causes joined components within the fluid to separate, kills undesirable organisms within the fluid, promotes interaction of components within the fluid and improves combustion of a liquid fuel. The fluid and components may also be subjected to abrasion and centrifugal and impact forces for separating the components, purifying the fluid, promoting interaction of the components and improving combustion.

28 Claims, 10 Drawing Sheets

U.S. PATENT DOCUMENTS

| | | | |
|---|---|---|---|
| 5,492,654 A | 2/1996 | Kozjuk et al. | |
| 5,717,181 A | 2/1998 | Colgate | |
| 5,810,052 A | 9/1998 | Kozyuk | |
| 5,914,027 A | 6/1999 | Ellingsen | |
| 5,931,771 A | 8/1999 | Kozyuk | |
| 5,937,906 A | 8/1999 | Kozyuk | |
| 5,969,207 A | 10/1999 | Kozyuk | |
| 5,971,601 A | 10/1999 | Kozyuk | |
| 6,012,492 A | 1/2000 | Kozyuk | |
| 6,019,947 A | 2/2000 | Kucherov | |
| 6,035,897 A | 3/2000 | Kozyuk | |
| 6,365,555 B1 | 4/2002 | Moser et al. | |
| 6,502,979 B1 | 1/2003 | Kozyuk | |
| 6,589,501 B2 | 7/2003 | Moser et al. | |
| 6,802,639 B2 | 10/2004 | Kozyuk | |
| 6,857,774 B2 * | 2/2005 | Kozyuk | 366/263 |
| 6,869,586 B1 | 3/2005 | Moser et al. | |
| 7,041,144 B2 | 5/2006 | Kozyuk | |
| 7,086,777 B2 | 8/2006 | Kozyuk | |
| 7,178,975 B2 | 2/2007 | Kozyuk | |
| 7,207,712 B2 | 4/2007 | Kozyuk | |
| 7,247,244 B2 | 7/2007 | Kozyuk | |
| 7,314,306 B2 | 1/2008 | Kozyuk | |
| 7,314,516 B2 | 1/2008 | Kozyuk et al. | |
| 7,338,551 B2 | 3/2008 | Kozyuk | |
| 7,357,566 B2 | 4/2008 | Kozyuk | |
| 7,452,425 B1 * | 11/2008 | Langhauser | 127/40 |
| 2004/0022122 A1 | 2/2004 | Kozyuk | |
| 2004/0042336 A1 | 3/2004 | Kozyuk | |
| 2005/0118692 A1 * | 6/2005 | Kinley et al. | 435/161 |
| 2005/0186315 A1 * | 8/2005 | Iiyama et al. | 426/518 |
| 2005/0233030 A1 * | 10/2005 | Lewis et al. | 426/49 |
| 2005/0237855 A1 * | 10/2005 | Kozyuk | 366/304 |
| 2006/0050608 A1 | 3/2006 | Kozyuk | |
| 2006/0081501 A1 | 4/2006 | Kozyuk | |
| 2006/0187748 A1 | 8/2006 | Kozyuk | |
| 2006/0251829 A1 | 11/2006 | Braun et al. | |
| 2006/0283788 A1 | 12/2006 | Schreppel, Jr. | |
| 2007/0193874 A1 * | 8/2007 | Adiga et al. | 203/99 |
| 2008/0011597 A1 * | 1/2008 | Spani | 202/84 |
| 2008/0144431 A1 | 6/2008 | Troxler | |
| 2008/0277264 A1 * | 11/2008 | Sprague | 204/157.9 |
| 2008/0281131 A1 * | 11/2008 | Kozyuk | 568/840 |
| 2010/0012583 A1 * | 1/2010 | Stuart | 210/633 |
| 2010/0112125 A1 * | 5/2010 | Kozyuk | 426/18 |

FOREIGN PATENT DOCUMENTS

| | | |
|---|---|---|
| GB | 2382787 | 6/2003 |
| WO | WO 98/11983 | 3/1998 |
| WO | WO 2005/058073 A1 | 6/2005 |
| WO | WO 2006/066421 A1 | 6/2006 |

OTHER PUBLICATIONS

Kinematica AG, Megatron System MT-V 1-65/MT-V 3-65, pp. 1-4, May 2003, Switzerland.

Kinematica AG, Megatron System MT 3000, pp. 1-4, Nov. 2002, Switzerland.

European Nano Systems 2005, Thomas Hielscher, Ultrasonic Production of Nano-Size Dispersions and Emulsions, pp. 138-143, Dec. 2005, Paris, France.

* cited by examiner

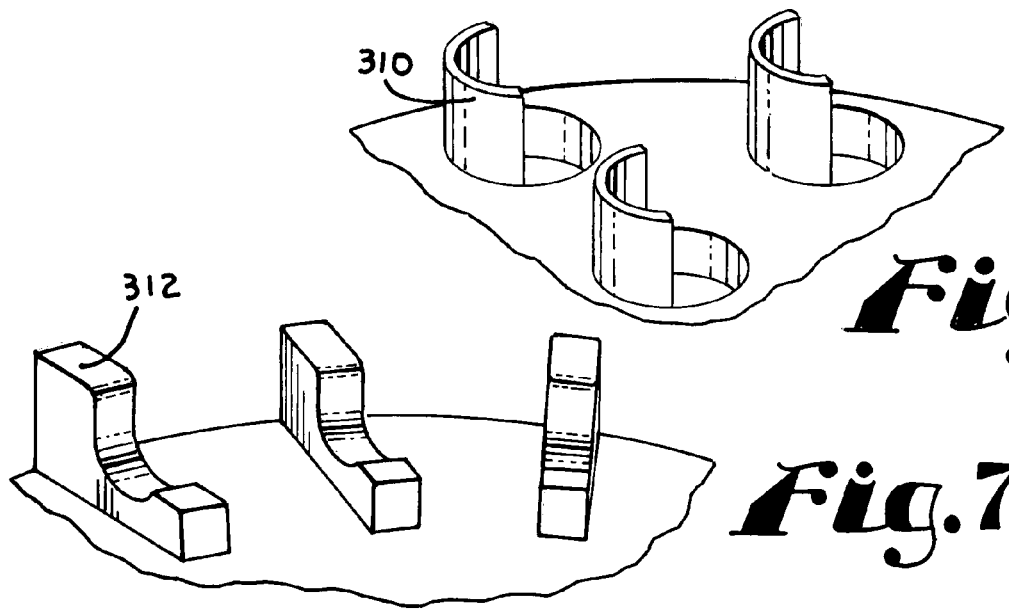
Fig.6.
Fig.7.
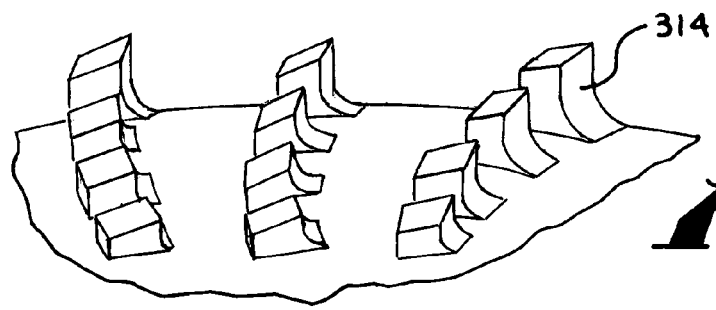
Fig.8.
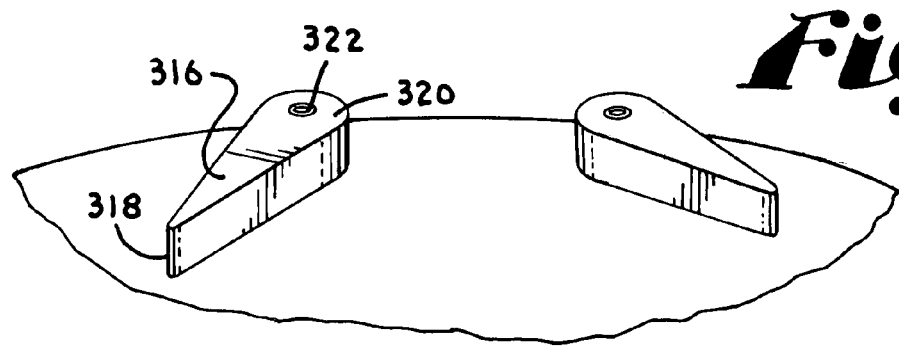
Fig.9.

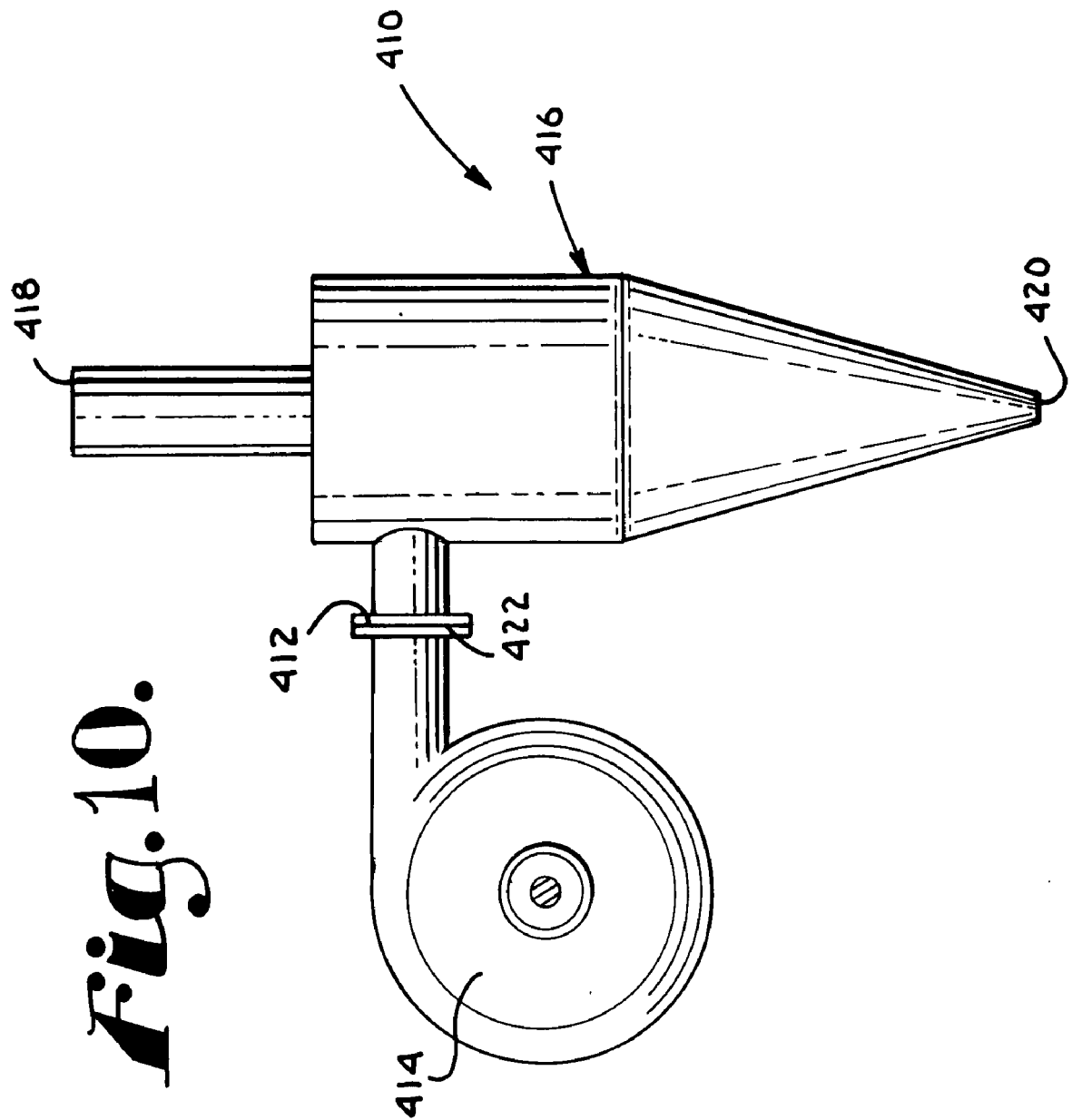

METHOD AND APPARATUS FOR SEPARATING, PURIFYING, PROMOTING INTERACTION AND IMPROVING COMBUSTION

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present invention is related in general to a method and apparatus for separating, purifying, promoting interaction and improving combustion and more particularly to a method and apparatus for separating joined components placed in a fluid medium, for purifying liquid, for promoting interaction between two or more components and improving combustion in a liquid fuel.

2. Description of Related Art

It has long been desirable to quickly separate joined components without degradation of the individual components. Examples of joined components needing separation include grain components, contaminants from pure products, juice from solid biomass, and starch and protein from biomass. Corn, in particular, is a grain that is desirable to separate into its individual components without degrading the components. Corn endosperm is rich in starch and protein which are both valuable as separate components.

A typical process for separating or milling corn includes fermenting (steeping) the kernels in warm water and sulfur dioxide for about 35 to 50 hours. The fermentation process softens the corn for easier separation by mechanical processing, but it also degrades the components of the corn. Some of the components of the kernels typically dissolve or suspend in the acidic water and are subsequently discarded. Discarding these components results in less profit for the corn miller. Additionally, at the end of the milling process, the corn requires substantial drying due to the fermentation process.

After fermentation, a degerminator separates the germ, pericarp and endosperm through abrasion between the corn and degerminator, abrasion between the individual corn kernels and impact between the corn and degerminator. Conventional degerminators frequently break the germ and do not consistently provide complete separation of germ and endosperm. Conventional degerminators also do not separate the starch and protein within the endosperm. Thus, a typical corn milling process is relatively expensive, time consuming and inefficient.

Purification of liquids to remove microorganisms is typically conducted using one of the following methods: distillation, filtration, boiling, disinfection by chemical treatment, ultraviolet light treatment or reverse osmosis. However, all of these processes have drawbacks including: expense, time, size, effectiveness and inefficiency. Pasteurization is one purification process used to kill microorganisms in liquids such as juice and milk. Pasteurization kills microorganisms by heating the liquid for a pre-determined amount of time. However, pasteurization does not kill all microorganisms within a liquid because to do so with heat alters the liquid's taste.

Promoting interaction between two or more components is desirable for promoting reactions between the components. Interaction between components is typically accomplished using an agitator or mixer which rotates a blade through the components and/or vibrates the components.

Improving combustion of a liquid fuel is desirable for improving efficiency and decreasing environmentally harmful exhaust emissions. Combustion of a liquid fuel is typically improved by atomizing the fuel to maximize its surface area. One conventional method for improving combustion is to utilize a fuel injector with a nozzle capable of atomizing the fuel.

BRIEF SUMMARY OF THE INVENTION

The invention claimed herein is a method and apparatus for separating, purifying, promoting interaction and improving combustion. The apparatus for separating, purifying, promoting interaction and improving combustion comprises a housing with an interior chamber, a rotor inside the chamber, a plurality of protrusions extending from the rotor, a shaft coupled with the rotor, and a prime mover for rotating the shaft and rotor. The housing has an inlet and outlet for allowing fluid to enter and exit the chamber. Preferably, the rotor rotates at a speed sufficient to cause cavitation of the fluid within the chamber and subject the fluid to a centrifugal force. Cavitation, abrasion, and centrifugal and impact forces preferably contribute to separating joined components placed within the fluid, killing undesirable organisms within the fluid, promoting interaction between two or more components placed within the fluid, and/or improving combustion of liquid fuel, whichever is desired.

The method of separating joined components includes the steps of placing the joined components in a fluid medium and inducing cavitation within the fluid to separate the joined components. The separation method may be used for any type of joined components, is quick, has low power requirements, and is capable of being performed with relatively inexpensive equipment.

The method of purifying liquid comprises inducing cavitation within the liquid to kill undesirable organisms within the liquid. The purification method kills undesirable microorganisms without altering the liquid's taste and other desirable biochemical characteristics.

The method of promoting interaction between two or more components includes the steps of placing the components in a fluid medium and subjecting the components to cavitation to promote interaction. In the preferred embodiment, the components may also be subjected to centrifugal force, abrasion and impact to promote interaction.

The method of improving combustion of a liquid fuel comprises inducing cavitation within the liquid fuel to vaporize the liquid fuel. The vaporized fuel combusts more completely within a combustion chamber than its liquid counterpart.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

BRIEF DESCRIPTION OF THE DRAWINGS

FIG. 6 is a perspective view of a portion of a rotor with C-shaped protrusions;

FIG. 7 is a perspective view of a portion of a rotor with J-shaped protrusions;

FIG. 8 is a perspective view of a portion of a rotor having tooth-like protrusions arranged in an arc;

FIG. 9 is a perspective view of a portion of a rotor having rotational protrusions;

FIG. 10 is a front elevational view of an alternative embodiment of an apparatus according to the present invention, showing a hydrocyclone coupled with the housing outlet;

DETAILED DESCRIPTION OF PREFERRED EMBODIMENT

Figure 1:
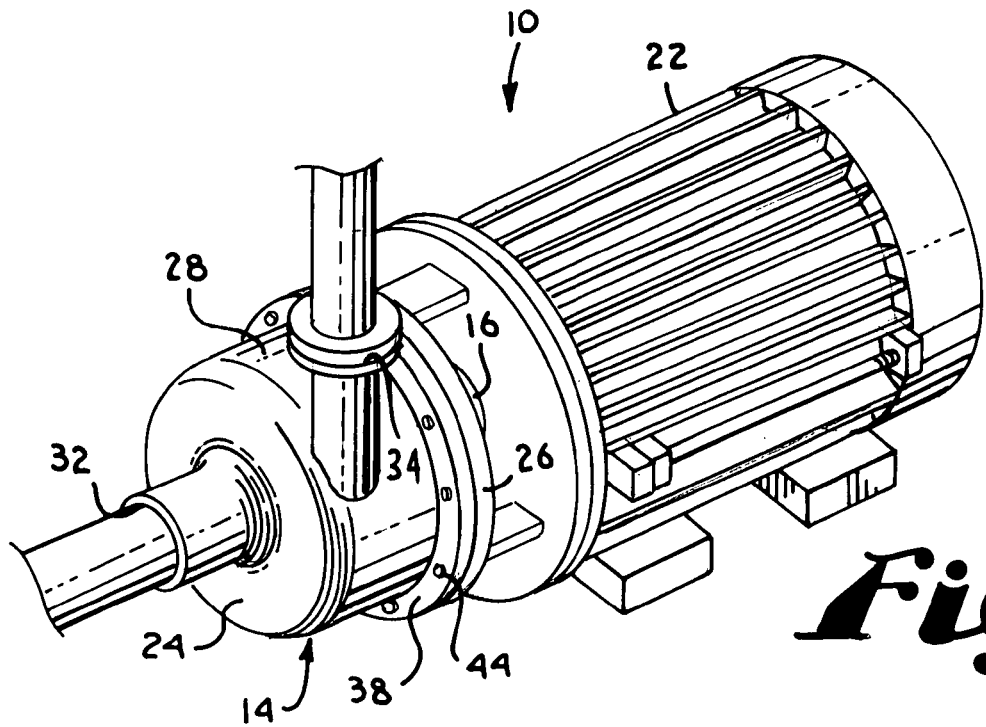
FIG. 1 is a perspective view of an apparatus according to the present invention.
Figure 2:
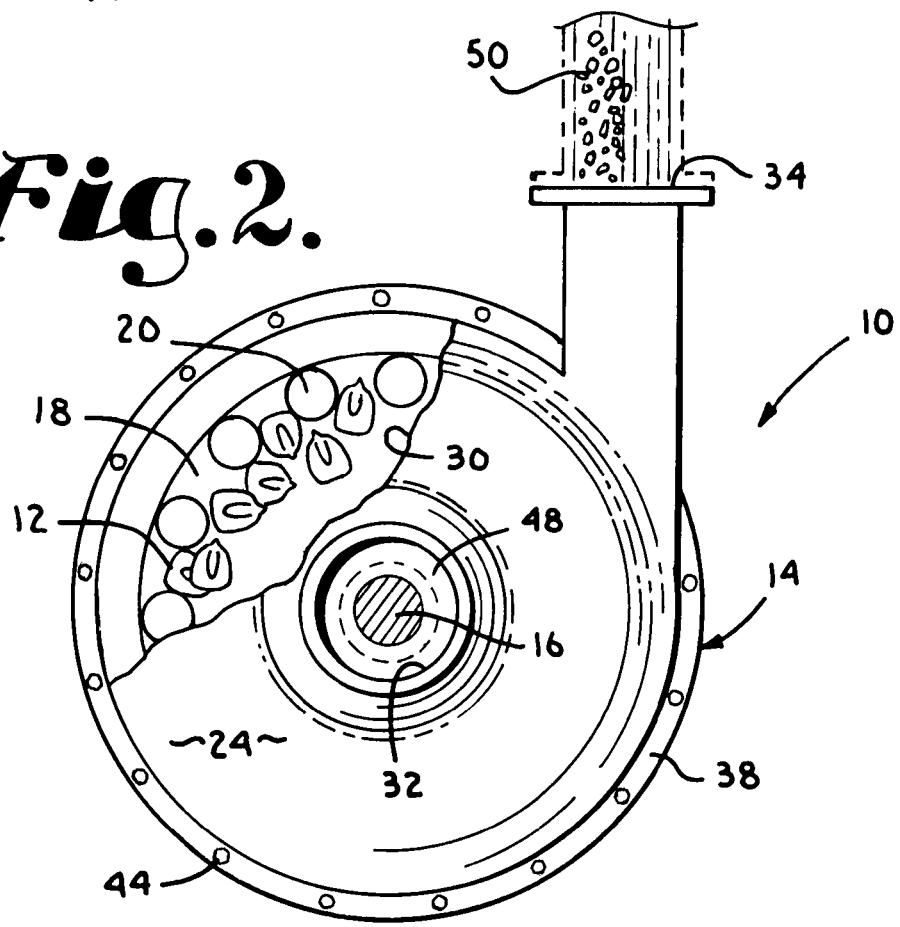
FIG. 2 is a front elevational view, with portions broken away, of the apparatus of FIG. 1.
Figure 3:
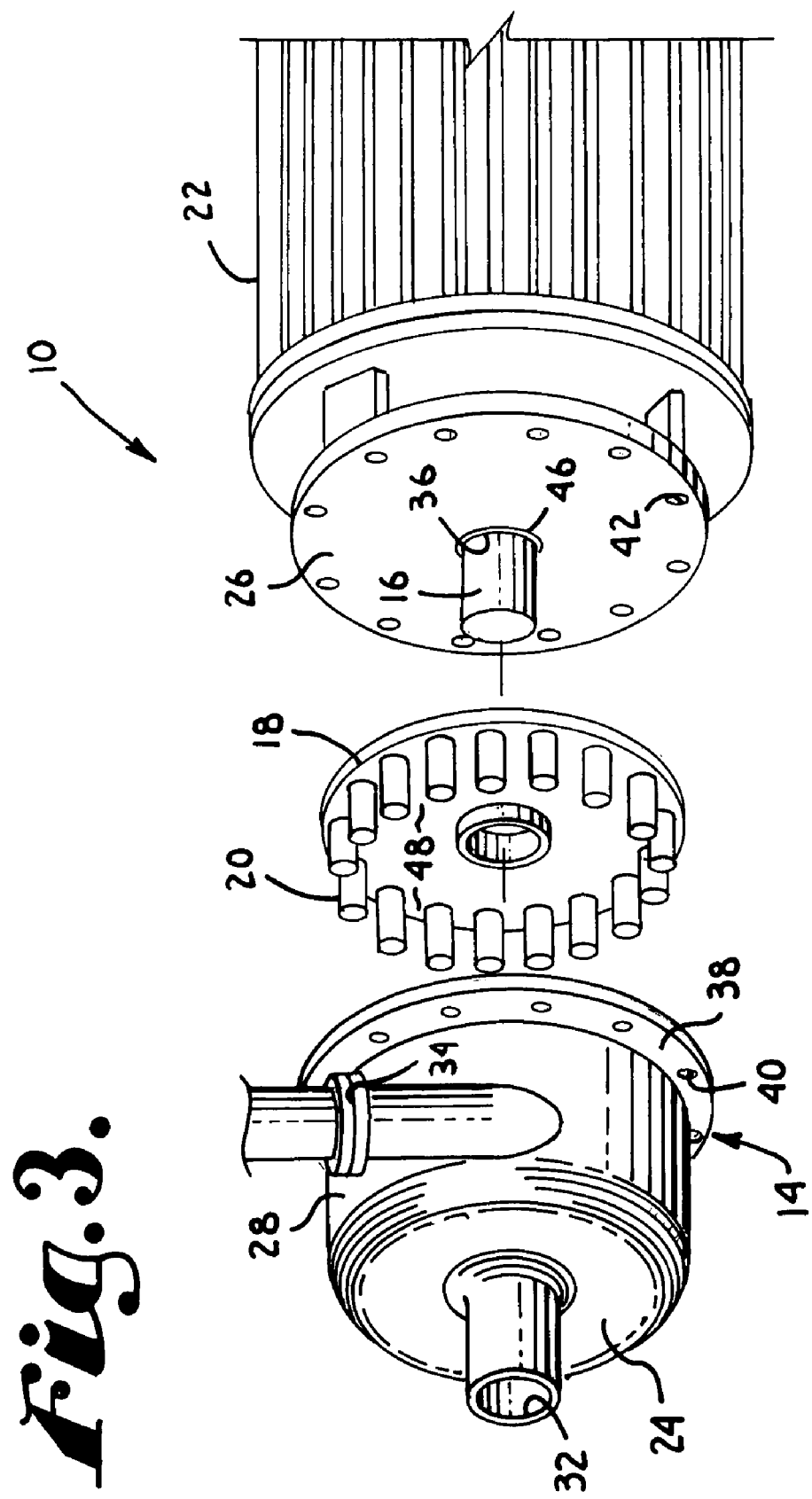
FIG. 3 is an exploded perspective view of the apparatus of FIG. 1.

FIGS. 1-3 show an apparatus 10 adapted to separate joined components placed in a fluid medium, purify liquid, promote interaction between two or more components placed in a fluid medium, and improve combustion of a liquid fuel. FIG. 2 shows the apparatus separating joined components. The joined components shown are the endosperm, germ and pericarp of corn kernels 12. Although FIG. 2 shows apparatus 10 separating corn, any joined component may be separated by the apparatus. Further, although FIG. 2 shows apparatus functioning as a separator, the apparatus also purifies liquid, promotes interaction between two or more components, and improves combustion of a liquid fuel. FIGS. 1-3 show the apparatus with a housing 14, a shaft 16, a circular rotor 18, protrusions 20 extending from rotor 18, and a motor 22 coupled with shaft 16.

FIGS. 2 and 3 show housing 14 with a first end wall 24, a second end wall 26, and a side wall 28 defining an interior cavitation chamber 30. FIGS. 1-3 show housing 14 with an inlet 32 in first end wall 24 adapted to allow fluid and components to enter chamber 30, and an outlet 34 in side wall 28 adapted to allow fluid and components to exit chamber 30. Inlet 32 may be coupled with a hopper (not shown) containing components, liquid or both. FIG. 3 shows a shaft opening 36 in second end wall 26. Shaft 16 projects into chamber 30 through shaft opening 36. FIGS. 1-3 show a flange 38 extending from side wall 28. FIG. 3 shows openings 40 in flange 38 which are aligned with openings 42 in second end wall 26. FIG. 1 shows bolts 44 securing flange 38 with second end wall 26. A seal (not shown) is preferably placed between flange 38 and second end wall 26, and a seal 46, shown in FIG. 3, is placed between shaft 16 and second end wall 26 to prevent fluid from leaking out of chamber 30.

FIG. 2 shows rotor 18 coupled with shaft 16 inside chamber 30. Rotor 18 has a front surface 48 facing inlet 32. Cylindrical protrusions 20 extend from front surface 48 toward inlet 32. All of the protrusions 20 are equidistant from the center of rotor 18 adjacent the peripheral edge of front surface 48. The spacing between adjoining protrusions 20 determines the length of time that components are retained within chamber 30. Protrusions spaced closer together will retain components within the chamber for a longer period of time than protrusions spaced farther apart. The longer the components are retained within the chamber, the greater the likelihood that the components will separate or interact, whichever is preferred. Preferably, the protrusions are spaced a distance sufficient to retain components within the housing or chamber until the components separate or interact. FIG. 2 shows adjoining protrusions 20 spaced a distance sufficient to retain corn kernels 12 within chamber 30 until separation of the germ, pericarp and endosperm. Preferably, the space between adjoining protrusions 20 is approximately 6 to 12 millimeters. The spacing between protrusions also affects the number of impacts between the components and the protrusions. More impacts between the components and the protrusions occur as the protrusions are spaced closer together. Therefore, if less impacts are desired the distance between protrusions should be increased. Although cylindrical protrusions 20 mounted equidistant from the rotor's center are shown, any type of protrusions mounted in any pattern on the rotor are within the scope of the invention.

FIG. 2 shows separation of the endosperm, germ and pericarp of corn kernels 12 placed in a fluid medium. Motor 22, shown in FIGS. 1 and 3, rotates shaft 16 and rotor 18 at a speed sufficient to cause cavitation within the fluid. The endosperm, germ and pericarp are separated by the combined effects of the rapid creation and implosion of the cavitation bubbles formed within the fluid, abrasion between the fluid and corn components, abrasion between the corn components, impacts between the corn components and protrusions 20, and centrifugal force. Before separation, the corn is retained within housing 14 by protrusions 20. While the corn is retained by protrusions 20, the fluid flows by the corn at high speed causing fluid abrasion on the corn's surface. The corn kernels 12 also rotate with respect to rotor 18 causing abrasion between the kernels. Each kernel 12 also impinges the protrusions 20. All of these factors contribute to separating the corn 12 into its components. FIG. 2 shows the separated components 50 exiting outlet 34. Although separation of corn is shown in FIG. 2, any type of joined component may be separated with apparatus 10, and the apparatus may also be used to purify liquid, promote interaction between two or more components in a fluid medium, and improve combustion of a liquid fuel.

Figure 4:
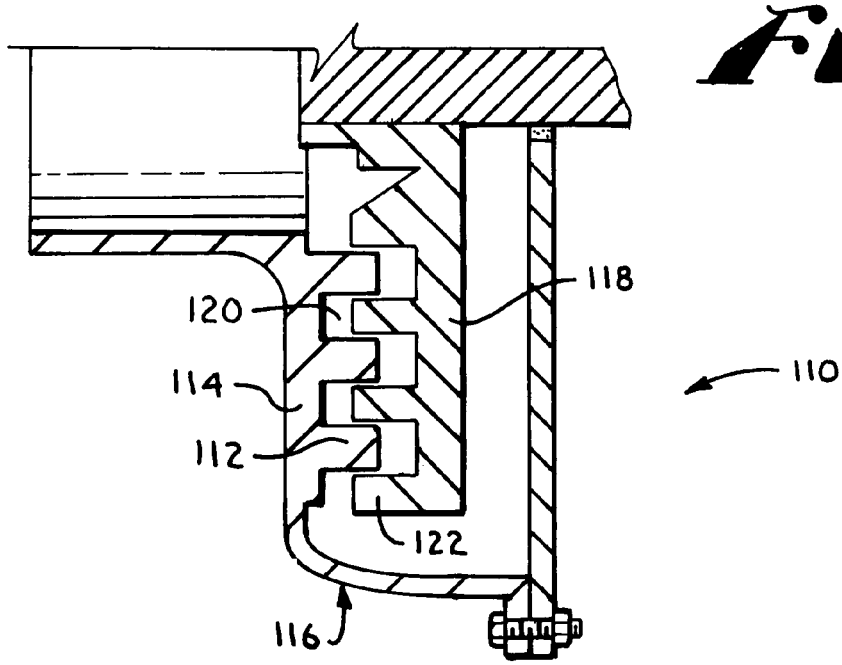
FIG. 4 is a partial cross sectional view of an alternative embodiment of an apparatus according to the present invention, showing a housing having protrusions.

FIG. 4 shows an alternative embodiment of an apparatus 110 according to the present invention. Apparatus 110 is substantially the same as apparatus 10 described above in connection with FIGS. 1-3 except that apparatus 110 has protrusions 112 extending from first end wall 114 of housing 116 toward rotor 118. Three circular rows of protrusions 112 extend from first end wall 114. There are gaps 120 between adjacent rows. Rotor 118 has four rows of protrusions 122 which are spaced a distance from the rotor's center such that the rows align with gaps 120.

Figure 5:
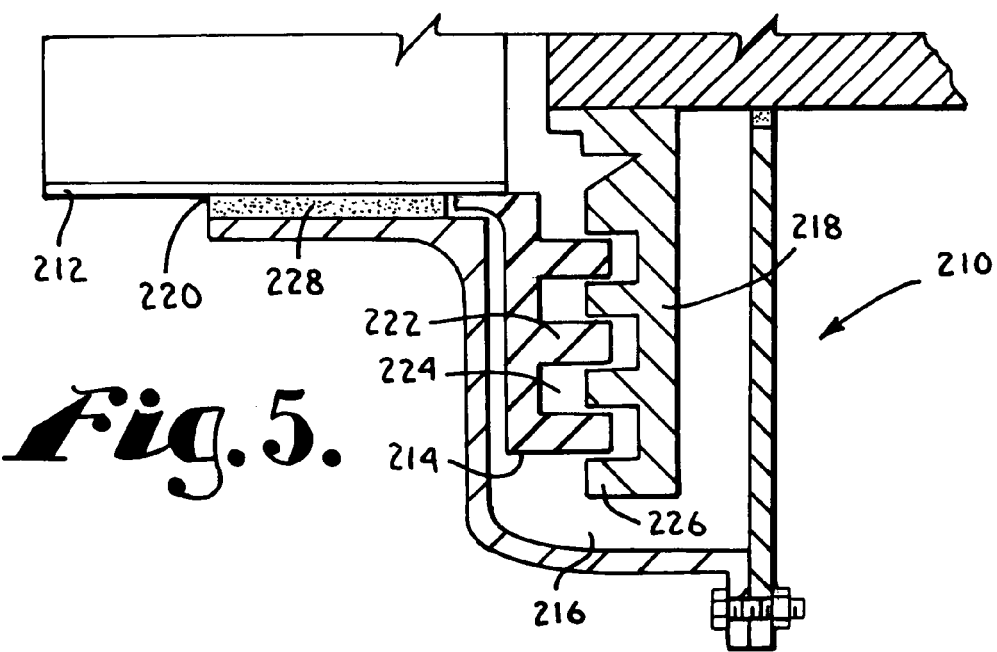
FIG. 5 is a partial cross sectional view of another alternative embodiment of an apparatus according to the present invention, showing a rotor and counter-rotor.

FIG. 5 shows another alternative embodiment of an apparatus 210 according to the present invention. Apparatus 210 is substantially the same as the apparatus 10 described above in connection with FIGS. 1-3 except that apparatus 210 has a tube 212 and a counter-rotor 214 coupled with tube 212 inside of interior chamber 216. Counter-rotor 214 has a front surface facing the front surface of rotor 218. Tube 212 is received by inlet 220 and extends into chamber 216. Three circular rows of protrusions 222 extend from the front surface of counter-rotor 214 toward rotor 218. There are gaps 224 between adjacent rows. Rotor 218 has four rows of protrusions 226 which are spaced a distance from the rotor's center such that the rows align with gaps 224. A seal 228 is positioned between tube 212 and inlet 220 for preventing fluid from leaking out of chamber 216. A drive mechanism (not shown), such as a belt, may be coupled with tube 212 outside chamber 216 for rotating tube 212 and counter-rotor 214. Although apparatuses 110 and 210 are shown in FIGS. 4 and 5 with circular rows of protrusions, the rows on housing, rotor and counter-rotor may have any configuration permitting the rotor to rotate within the housing.

FIGS. 6-9 show examples of protrusions that may be used with any of the apparatuses 10, 110 and 210 described above in connection with FIGS. 1-5. FIG. 6 shows protrusions 310 having a C-shaped top profile. The protrusions are hollow and are arranged in two rows on the rotor. C-shaped protrusions 310 are preferably used when it is desirable to induce high levels of cavitation in the fluid. FIG. 7 shows protrusions 312 having a J-shaped side profile. J-shaped protrusions 312 are positioned adjacent a peripheral edge of the front surface of the rotor. FIG. 8 shows four rows of spaced apart tooth-like protrusions 314. The rows are positioned in offset relationship such that the protrusions 314 form a radial curved pattern. FIG. 9 shows rotating protrusions 316. The protrusions 316 have a free end 318 and a fixed end 320 rotatably mounted on the front surface of the rotor. The fixed end 320 has an opening which receives a pin 322 extending from the rotor. The invention described herein is not limited to any particular type of protrusions, or any particular pattern of protrusions. All protrusions and patterns shown herein are exemplary only.

FIG. 10 shows an alternative embodiment of an apparatus 410 according to the present invention. Apparatus 410 is substantially identical to the apparatuses 10, 110 and 210 described in connection with the embodiments shown in FIGS. 1-5 except that outlet 412 of housing 414 is coupled with a hydrocyclone 416, or centrifuge. Hydrocyclone 416 has the general shape of an inverted cone with a cylinder extending upward from the base of the cone. Hydrocyclone 416 has a top outlet 418, a bottom outlet 420 and an inlet 422 coupled with housing outlet 412. Inlet 422 is positioned near the top of hydrocyclone 416.

In operation, motor 22 of apparatus 10, shown in FIGS. 1-3, is powered on. Inlet 32 receives joined components placed in fluid, unpurified liquid, two or more components placed in fluid, or liquid fuel. The joined components placed in fluid, unpurified liquid, two or more components placed in fluid, or liquid fuel enter chamber 30. Motor 22 rotates shaft 16 and rotor 18 at a speed sufficient to cause cavitation of the fluid within chamber 30 as protrusions 20 move through the fluid. The speed of shaft rotation is preferably between 500 to 10,000 revolutions per minute.

The fluid cavitates due to the reduction in fluid pressure behind protrusions 20 as the protrusions move through the fluid. The fluid cavitates from a liquid to a gas when the fluid pressure behind protrusions 20 is reduced to below the liquid's vapor pressure. A plurality of gas bubbles form within the fluid due to cavitation. These gas bubbles move from the low pressure area of formation into an area of chamber 30 with higher fluid pressure. Upon entering a region of fluid pressure greater than the vapor pressure of the liquid, the gas bubbles collapse. This creation and collapse, or implosion, of gas bubbles creates ultrasonic waves within chamber 30. The power of the ultrasonic waves has been measured at the outside of housing 14 as being between about 40 dB to about 60 dB by a well known cavitation implosion measuring device sold under the trademark Vibrotip®. The ultrasonic waves are a primary factor in separating joined components within a fluid medium, in purifying liquid by killing undesirable organisms within the liquid, in promoting interaction between two or more components, and in improving combustion of liquid fuel by vaporizing the liquid fuel.

Additional forces within chamber 30 contribute to separating joined components within a fluid medium, purifying liquid, promoting interaction between two or more components in a fluid medium, and improving combustion of a liquid fuel. These forces include centrifugal force resulting from rotating rotor 18 within the fluid, abrasion between the fluid and components, abrasion between the components, and impacts between the components and protrusions 20. The combined effects of these factors contribute to separating joined components placed within a fluid, purifying liquid, promoting interaction between two or more components placed within a fluid, and improving combustion of a liquid fuel. The separated components and fluid, purified liquid, interacted components and fluid, or liquid fuel exit chamber 30 through outlet 34.

Apparatus 110 shown in FIG. 4 operates in the same way as described above for apparatus 10 shown in FIGS. 1-3. Apparatus 210 shown in FIG. 5 operates in substantially the same manner as apparatus 10 shown in FIGS. 1-3 except that apparatus 210 has a rotating tube 212 and counter-rotor 214. A drive mechanism (not shown) coupled with tube 212 rotates tube 212 and counter-rotor 214. Tube 212 and counter-rotor 214 preferably rotate in a direction opposite to the direction of rotation of rotor 218, but it is within the scope of the invention for rotor 218 and counter-rotor 214 to rotate in the same direction. The components and fluid enter chamber 216 through tube 212.

Apparatus 410 shown in FIG. 10 has a housing 414 with a rotor that operates in the same manner as any of the apparatuses 10, 110 and 210 described in FIGS. 1-5. However, after the fluid and components exit outlet 412 they enter hydrocyclone 416. Fluid and components exiting outlet 412 and entering hydrocyclone 416 rotate around the interior wall of hydrocyclone 416. The rotation subjects the fluid and components to a centrifugal force which divides the components based on density. Heavier components move outward toward the interior wall of hydrocyclone 416 and spiral down the wall to bottom outlet 420. Lighter components move toward the center axis of hydrocyclone 416 and exit through top outlet 418. Thus, hydrocyclone 416 divides components with different densities. Hydrocyclone 416 is particularly well suited to divide gas from liquid. A slight vacuum may be introduced at top outlet 418 to induce the lighter components to exit through top outlet 418.

Figure 11A:
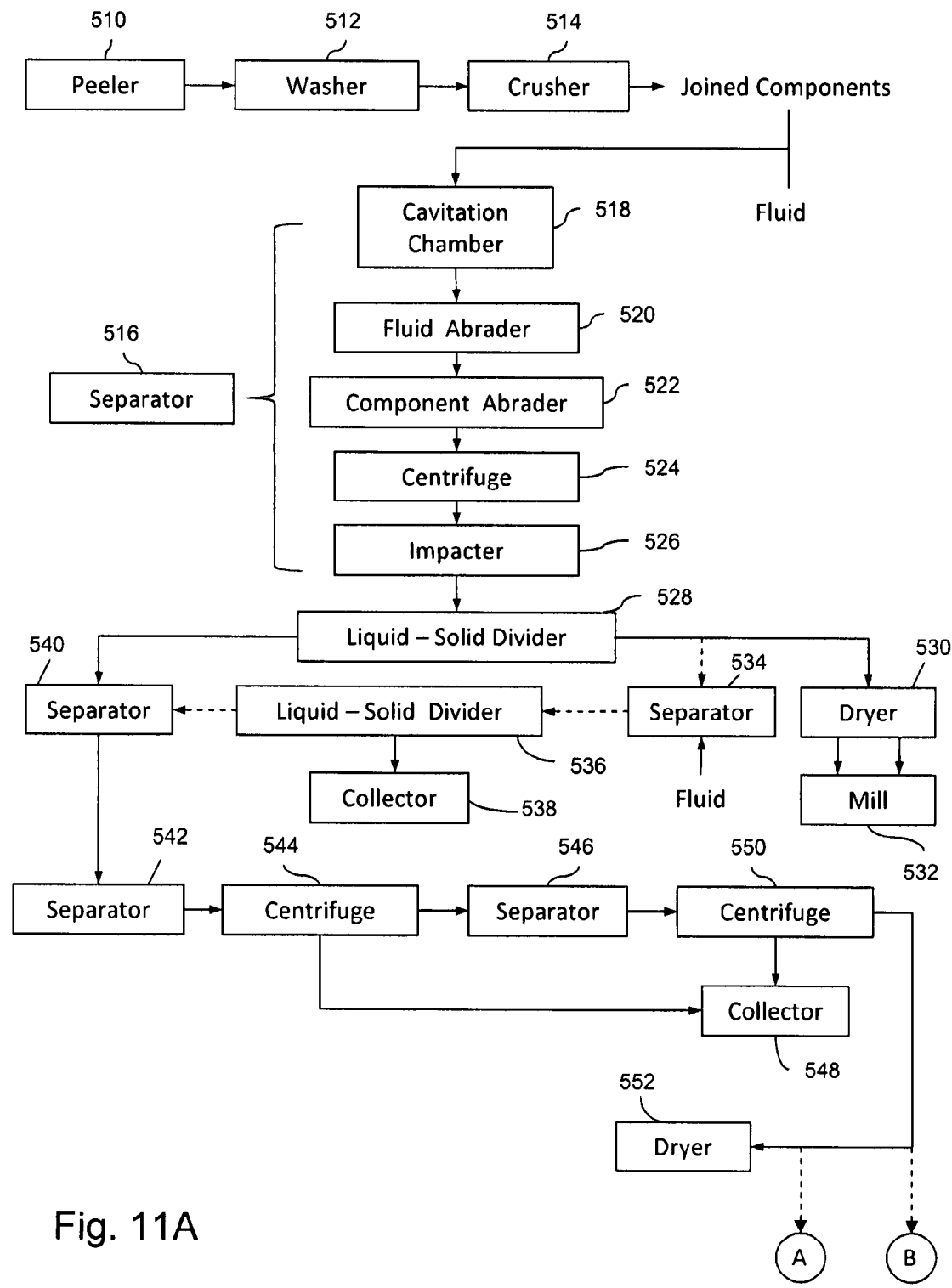
FIG. 11A is a flow diagram of a method of separation according to the present invention.
Figure 11B:
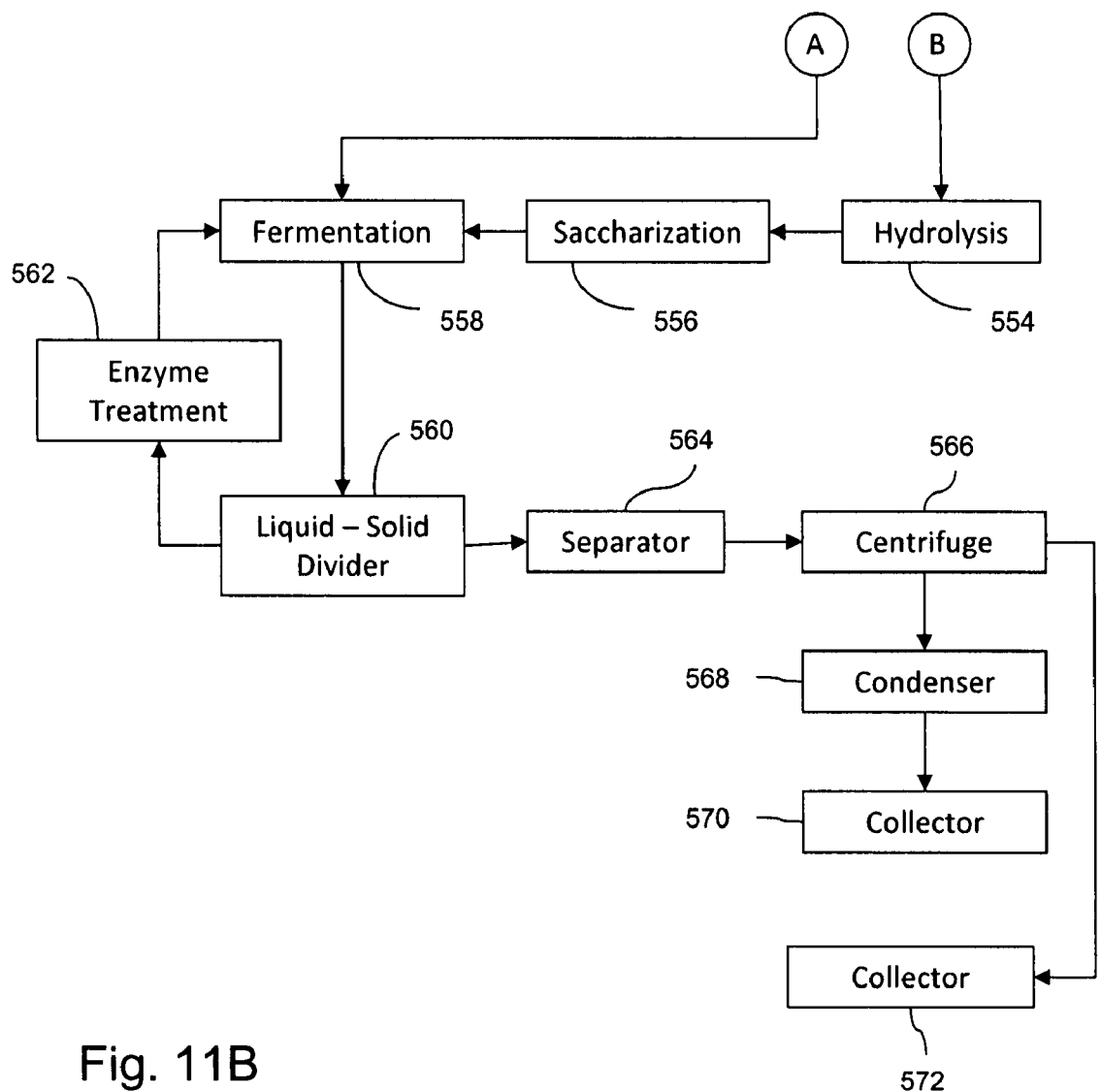
FIG. 11B is a continuation of the flow diagram of FIG. 11A.

FIGS. 11A and 11B show a method for separating joined components. If necessary, the joined components are peeled at 510, washed at 512 and/or crushed at 514 during the beginning of the separation process, as shown in FIG. 11A. The joined components are then placed in a fluid medium and sent to a first separator 516. First separator 516 has a cavitation chamber 518, a fluid abrader 520, a component abrader 522, a centrifuge 524 and an impactor 526. The separator may have a structure as any of the apparatuses 10, 110 and 210 described above, and it should be appreciated that the same structure may perform steps 518-526 simultaneously.

In the cavitation chamber 518, cavitation is induced in the fluid as described above in connection with apparatus 10 shown in FIGS. 1-3. The ultrasonic waves resulting from the creation and implosion of cavitation bubbles within the fluid is one factor in separating the joined components. The other steps in separator 516 are also factors in separating the joined components. Fluid abrader 520 induces abrasion between the fluid and joined components and component abrader 522 induces abrasion between the joined components to separate the components. Abrasion between the joined components may be abrasion between the individual components, or it may be abrasion between discrete units of joined components. Centrifuge 524 subjects the joined components to centrifugal force and impactor 526 subjects the joined components to impact forces to separate the components. After separation, the components are positioned throughout the fluid medium.

The separated components exit separator 516 and go to liquid-solid divider 528 which divides relatively large solid components from the fluid medium. Solid components of fine granulometry form a suspension with the fluid and are not divided from the fluid by liquid-solid divider 528. Liquid-solid divider 528 may be a sieve or any other suitable apparatus for dividing solids from liquid. The solid components divided from the fluid medium are dried by dryer 530 which also has the capability to further separate the solid components. The solid components are then ground in a mill 532 to a desired size. Alternatively, the solid components exiting liquid-solid divider 528 are placed in a fluid medium and sent to separator 534, where the same steps occur as in separator 516. Separator 534 further separates the solid components in the manner as described above with respect to separator 516. The fluid and separated solid components go to liquid-solid divider 536 where relatively large solid components are divided from the fluid and sent to a collector 538. Solid components of fine granulometry form a suspension with the fluid and are not divided from the fluid by liquid-solid divider 536. The suspensions of fluid and solid components of fine granulometry exiting liquid-solid dividers 528 and 536 combine at separator 540.

Separator 540 performs the same steps as separator 516 and further separates joined components within the fluid. The fluid and components exiting separator 540 flow into separator 542 which performs the same steps as separator 516. Separator 542 further separates the joined components within the fluid. The fluid and components exiting separator 542 flow into centrifuge 544, which may have a structure as the hydrocyclone described above in connection with FIG. 10. Centrifuge 544 subjects the fluid and components to a centrifugal force to divide the components based on density. Heavier components exiting centrifuge 544 go to separator 546, while lighter components exiting centrifuge 544 go to collector 548. After exiting separator 546, the heavier components enter centrifuge 550 which again divides the components based on density. Heavier components exiting centrifuge 550 go to a dryer 552, while lighter components go to collector 548. Either of the heavier or the lighter components may be further processed to achieve a desired end product.

If the resulting heavier components are starch or sugar, then instead of going to dryer 552, they may undergo an alternate process shown in FIG. 11B to convert the starch or sugar into ethanol. For ethanol production, starch exiting centrifuge 550, shown in FIG. 11A, follows path B to undergo hydrolysis, or liquefaction, at station 554, shown in FIG. 11B. Sugar exiting centrifuge 550, shown in FIG. 11A, follows path A to undergo fermentation at station 558, shown in FIG. 11B. For starch, at station 554 it is heated and joined with enzymes to promote hydrolysis. The hydrolyzed starch is then joined with enzymes and undergoes saccharization at station 556 where the hydrolyzed starch is converted into sugar syrup. The hydrolysis at station 554 and saccharization at station 556 may each be performed by any of the apparatuses 10, 110 and 210 shown in FIGS. 1-5, and according to the method of promoting interaction shown in FIG. 13 and described below in connection with FIG. 13.

The sugar syrup exiting station 556 is joined with yeast and undergoes fermentation at station 558 (the step where sugar exiting centrifuge 550 begins). Fermentation of the sugar syrup produces liquid ethanol. A heat exchanger (not shown) may be coupled with the apparatus performing fermentation step 558 for removing heat from the apparatus. After fermentation, the liquid ethanol goes to liquid-solid divider 560. Solids remaining in the liquid ethanol are divided from the ethanol and undergo enzyme treatment at step 562 to hydrolyze and saccharize the solids converting them to sugar syrup. This sugar then undergoes fermentation at station 558. Step 562 may be performed in a substantially similar manner as steps 554 and 556.

Liquid ethanol exiting liquid-solid divider 560 begins a distillation process at a separator 564, which has substantially the same configuration as separator 516. A heater (not shown) may be coupled with the separator 564 for heating the liquid. Preferably, the heater heats the liquid ethanol to approximately 80 degrees Celsius. The liquid ethanol may be heated before entering separator 564 by passing through a copper coil immersed in water heated by solar energy. Separator 564 induces cavitation within the liquid ethanol. The rapid creation and implosion of cavitation bubbles within the liquid ethanol converts it to ethanol vapor, however, some liquid may exit separator 564 with the ethanol vapor. The liquid remaining may be liquid ethanol and/or liquid added in a previous step that could not be converted into ethanol. The liquid and ethanol vapor exit separator 564 and go to centrifuge 566, which may have a structure similar to the hydrocyclone shown in FIG. 10. Centrifuge 566 subjects the liquid and ethanol vapor to a centrifugal force dividing the ethanol vapor from the liquid. Liquid exiting centrifuge 566 is collected by collector 572 where it is discarded or sent to undergo a second distillation process to recover any remaining ethanol within the liquid. The ethanol vapor exiting centrifuge 566 goes to a condenser 568 which condenses the vapor into a liquid. The liquid ethanol is collected by collector 570.

The joined components that are separated by the process shown in FIGS. 11A and 11B may be solids, liquids, gases or any combination of the three. For separating solids, the percent of solids in the fluid medium is preferably about 10-40% by volume. The separation process may be affected by varying the percent of solids placed within the fluid medium. A higher percentage of solids in the fluid medium results in increased abrasion between the solid components, but a decreased number of impacts between the protrusions and components. A lesser percentage of solids in the fluid medium results in decreased abrasion between the solid components, and an increased number of impacts between the protrusions and components. The percent by volume of solids in the fluid medium may be varied as necessary for optimal separation of the type of components being separated.

Other external factors which may affect the separation process shown in FIGS. 11A and 11B include the pH level, viscosity and temperature of the fluid medium or components. As the pH level moves from neutral to acidity or alkalinity, the hydrogen potential permits greater atomic activity which may accelerate separation. The forces (cavitation, fluid abrasion, component abrasion, centrifugal and impact) generated within the separators promote the atomic activity by fostering contact between the fluid medium and joined components. An increase in viscosity of the fluid medium reduces the effects of cavitation within the fluid by restricting the formation, implosion and movement of cavitation bubbles. An increase in temperature increases the effects of cavitation within the fluid by reducing the attraction of the molecules of the liquid and thereby increasing the vapor pressure of the fluid medium. Cavitation bubbles form more frequently when the vapor pressure of the fluid medium is increased because less reduction in pressure is necessary to reduce the fluid pressure below the increased vapor pressure.

The method of separating shown in FIGS. 11A and 11B may be used to separate the joined components of a corn kernel, namely, the endosperm, pericarp and germ. If desired the corn is peeled in peeler 510, washed in washer 512 and crushed in crusher 514 before it is sent to separator 516. Separator 516 separates the endosperm, germ and pericarp by the method described above. The endosperm has a fine granulometry and thus forms a suspension with the fluid after separation. Preferably, the mixture of fluid and corn kernels entering separator 516 is about 10 to 20% corn kernels by volume. Separator 516 preferably has a construction as apparatus 10 shown in FIGS. 1-3. For corn separation, the rotor preferably has one row of protrusions. The diameter of the row is preferably about 124 millimeters and the diameter of the protrusions about 9.5 millimeters. Preferably, the height of the protrusions is about 15 millimeters and the thickness of the rotor is about 10 millimeters. There is a distance of about 10 millimeters between protrusions. Preferably, the rotor rotates at a speed of between about 2500 to 4500 revolutions per minute, and in a most preferred embodiment at a speed of about 3600 revolutions per minute. The process of separating the endosperm, germ, and pericarp occurs within about two minutes. Also, it is not necessary to steep the corn kernels in water or an acidic solution before separation as it is in conventional separation processes.

For separating corn according to the method shown in FIGS. 11A and 11B, separator 516 could be replaced by a plurality of separators coupled together each having a structure similar to apparatus 10. In this configuration each subsequent separator in the series has a gradually reduced distance between protrusions. There may be eight coupled separators replacing separator 516, where the distance between protrusions is gradually reduced from 10 millimeters to 7.5 millimeters.

Liquid-solid divider 528 divides the germ and pericarp from the fluid and endosperm suspension after separation of the endosperm, germ and pericarp. The germ and pericarp go to dryer 530, which is preferably a pneumatic type 60 degrees Celsius hot air drying system having the capability to divide the pericarp from the germ. The pericarp and germ may then be ground separately at mill 532 to meet market requirements. The fluid and endosperm suspension goes to separator 540.

Separator 540 induces cavitation within the fluid and endosperm suspension in order to separate starch and protein from the endosperm cells. Preferably, separator 540 has a structure similar to apparatus 10 except for having a rotor with two rows of protrusions. Separators 542 and 546 each separate starch and protein that is joined. Centrifuges 544 and 550 divide the separated starch and protein. The centrifuges have preferably the same structure as the hydrocyclone shown in FIG. 10. Centrifuges 544 and 550 subject the separated starch and protein to a centrifugal force dividing the starch and protein. The starch, which is heavier than the protein, travels around the interior wall of centrifuges 544 and 550 and exits at the bottom of the centrifuges with the fluid. The protein exits through the top of the centrifuges 544 and 550 and goes to collector 548.

After exiting centrifuge 550, the starch may either go to dryer 552, or it may be hydrolyzed, saccharized, fermented and distilled for producing ethanol according to the steps described above and shown in FIG. 11B. The corn separation process described herein can recover 20% more ethanol from corn than any conventional corn ethanol production process because the starch is not degraded by steeping the corn kernels before separation. Further, the components retain their original characteristics because they are not crushed by a mill or degerminator before separation.

The method of separating shown in FIG. 11A may also be used for producing corn atole. Corn is placed in water and sent through separator 516 which separates the germ, pericarp and endosperm. Liquid-solid divider 528 divides the germ and pericarp from the fluid and endosperm suspension. The germ and pericarp go to dryer 530 and mill 532. The endosperm is digested and dried producing atole powder. Atole produced according to conventional methods contains sulfur because the corn is steeped in a sulfur solution. The atole produced according to the method described herein does not contain sulfur because the corn is not steeped in a sulfur solution. Therefore, atole produced according to the present method is healthier and tastes better than atole produced according to conventional methods.

Coffee berries may also be separated according to the method shown in FIG. 11A. The joined components of a coffee berry are the skin, pulp, mucilage, parchment and bean. Conventional processes for separating the components of a coffee berry require the steps of depulping the berry, fermenting the bean to loosen the mucilage, washing the bean to remove the mucilage, drying the bean, and shelling the bean to remove the parchment. It typically takes about 1 to 7 days to perform these steps. Separator 516 of the method shown in FIG. 11A separates the components of a coffee berry in only 7 to 10 seconds. Additionally, after a coffee berry is separated according to the method shown in FIG. 11A, the coffee bean needs less time to dry because it is exposed to water for less time than in a conventional process. The present method also produces higher quality coffee beans because they are neither subject to the crushing action of a depulping mill nor to a typical fermentation process. The current method for processing coffee costs about 30% less than conventional methods due to increased efficiency.

Preferably, for coffee separation the mixture of fluid to coffee berries is about 15 to 22% coffee berries by volume. Preferably, the first separator is an apparatus as shown in FIGS. 1-3 with a rotor as described below and a distance between protrusions about 50% greater than the longest coffee bean in order to ensure no beans are damaged. There are a variety of different rotors that are sufficient for coffee separation according to the method shown in FIG. 11A. One type of rotor has three rows of protrusions with each row having a respective diameter of 20 centimeters, 30 centimeters and 40 centimeters. The protrusions are cylindrical with a diameter of about 10 millimeters. The distance between the protrusions decreases from about 15 millimeters at the first row to about 10 millimeters at the third row. A second type of rotor has 19 cylindrical protrusions each having a diameter of about 0.375 inches. The protrusions are adjacent the peripheral edge of a rotor having a diameter of about 124 millimeters. There is a distance between protrusions of about 9 millimeters. A third type of rotor has 21 cylindrical protrusions each having a diameter of about 0.375 inches. The protrusions are adjacent the peripheral edge of a rotor having a diameter of about 124 millimeters. There is a distance between protrusions of about 7.5 millimeters. A fourth type of rotor has 20 protrusions with a C-shaped top profile, as shown in FIG. 6, each having a diameter of about 9.5 millimeters. The protrusions are adjacent the peripheral edge of a rotor having a diameter of about 124 millimeters. There is a distance between protrusions of about 7.5 millimeters. A fifth type of rotor has 14 protrusions with a C-shaped top profile, as shown in FIG. 6, each having a diameter of about 0.5 inches. The protrusions are adjacent the peripheral edge of a rotor having a diameter of about 124 millimeters. There is a distance between protrusions of about 16 millimeters. A sixth type of rotor has 20 conical protrusions each having a base diameter of about 12 millimeters and a crown diameter of about 4 millimeters. The protrusions are adjacent the peripheral edge of a rotor having a diameter of about 125 millimeters. A seventh type of rotor has 24 conical protrusions each having a base diameter of about 9.5 millimeters and a crown diameter of about 4 millimeters. The protrusions are adjacent the peripheral edge of a rotor having a diameter of about 124 millimeters.

After the beans, pulp, mucilage, pericarp and parchment of the coffee berries are separated by separator 516, the beans are divided from the pulp, mucilage, pericarp and parchment by a divider. The divider may be a sieve, or series of sieves designed to divide the various components based on size. The coffee beans are then dried, graded and packed for shipping. The pulp, mucilage, pericarp and parchment are sent to another separator preferably having a similar structure to apparatus 10 shown in FIGS. 1-3. The separated components then go to a divider which divides the pulp and mucilage from the parchment and pericarp. The pulp and mucilage may be fermented for production of ethanol as described above in connection with FIG. 11B, or used to produce methane gas. The parchment and pericarp preferably undergo an extraction process which extracts nutraceutic substances and/or fibers from the components.

The method shown in FIGS. 11A and 11B may also be used to separate the starch and cells of a cassava root. The cassava root is preferably peeled at peeler 510, washed at washer 512 and crushed at crusher 514 before being placed in water. The ratio of water and crushed cassava root is about 25 to 35% cassava root by volume. The cassava root is sent through separator 516 which preferably has a structure similar to apparatus 10 shown in FIGS. 1-3. After separator 516, starch separated from the solid cassava biomass forms a suspension with the water. The solid cassava biomass, water and starch go to liquid-solid divider 528 where the starch and water suspension is divided from the solid cassava biomass. The starch and water suspension goes to separator 540. The solid cassava biomass is placed in water and goes to separator 534 for further separation of starch and solid cassava biomass. Liquid-solid divider 536 divides the starch and water suspension exiting separator 534 from the solid cassava biomass. The solid cassava biomass goes to collector 538 and the starch and water suspension goes to separator 540 where it joins the starch and water suspension from divider 528. From separator 540, the process continues as described above with respect to separating corn. Preferably, the separators have rotors with protrusions having a diameter of about 9.5 millimeters and a distance between protrusions of about 10 millimeters. For separation of cassava root any of the separators may also have a dual-row rotor with a counter-rotor to improve breakdown of the root.

The method shown in FIGS. 11A and 11B may be used to separate sugar cane from sugar cane juice. The conventional process for recovering sugar cane juice from sugar cane comprises crushing or rolling the sugar cane to extract juice from the cane. Then, the cane is either discarded or recycled, where any cane juice still residing in the cane is lost. The method shown in FIGS. 11A and 11B retrieves about 9.5% sugar cane juice by weight from solid sugar cane that is discarded after a conventional cane juice extraction process.

According to the separation method of FIG. 11A, first, the sugar cane is crushed at crusher 514 and any sugar cane juice extracted during crushing is collected. Then, the crushed sugar cane is placed in water and sent through separator 516, which may have a structure similar to apparatus 10 shown in FIGS. 1-3. Preferably, the mixture of water and sugar cane is about 25 to 35% sugar cane by volume. Separator 516 separates the sugar cane juice from the sugar cane via the factors described above. Liquid-solid divider 528 divides the solid sugar cane from the water and cane juice. The solid sugar cane is again placed in water and sent through separator 534 which further separates sugar cane juice from the sugar cane. Liquid-solid divider 536 divides the sugar cane juice and sugar cane exiting separator 534. The solid sugar cane goes to collector 538 where it may be used as aggregate or in the production of paper. The sugar cane juice may be processed into crystalline sugar, or it may be fermented and distilled to produce ethanol as described above with respect to steps 558-572. Sugar beet juice may be separated from a sugar beet in the same manner as described above for separating sugar cane juice from sugar cane.

The method shown in FIG. 11A may also be used for separating gaseous impurities from liquids. For instance, the method may be used for separating sulfur dioxide, or other gaseous impurities, from liquid fuel. Sulfur dioxide is a compound present in fuel that is released into the atmosphere upon combustion and is harmful to both health and environment. For separating fuel and sulfur dioxide according to the method shown in FIG. 11A, fuel containing sulfur dioxide is sent directly to a separator coupled with a centrifuge such as 542 and 544. Preferably, apparatus 410 as shown in FIG. 10 is used for separation of the sulfur dioxide and fuel. The separator induces cavitation within the liquid fuel. Cavitation enhances the formation of sulfur dioxide gas bubbles within the fuel. The centrifuge subjects the fuel to centrifugal force dividing the sulfur dioxide gas from the liquid fuel. Preferably, the sulfur dioxide gas exits through the top of the centrifuge and the purified fuel exits through the bottom of the centrifuge. Both the gas and the fuel may be collected in a collector.

The method shown in FIG. 11A may also be used to separate soil and toxins from grain. For separation, grain covered in soil and toxins is placed in water and sent through separator 516. The separator separates the grain, soil and toxins. Liquid-solid divider 528 divides the clean grain from the soil and toxins, which remain suspended in the water. Liquid-solid divider 528 may be a sieve. The clean grain is dried in dryer 530 and processed as desired. The method may also be used to decontaminate wastewater by separating the water from contaminants. For instance, the method may be used to separate cyanogenic compounds from cassava starch processing wastewater.

The method shown in FIG. 11A may also be used for separating any components of vegetable or animal tissue. The vegetable or animal tissue is processed and selected, placed in water and sent through separator 516 for separation of the tissue components. The tissue components are then preferably divided by any method, washed, dried and packaged.

Soybeans may also be separated according to the method shown in FIG. 11A. The soybean separation method described herein greatly reduces the number of steps and equipment required by traditional methods. The joined components of soybeans are the shell, germ and endosperm. The soybeans are placed in water and sent through separator 516. Separator 516 separates the shell, germ and endosperm. Liquid-solid divider 528 may be used to divide the shell, germ and endosperm. Liquid-solid divider 528 may be a sieve or series of sieves sized to divide the components. The method may also be used to separate the joined components of other beans, grains such as sorghum, pineapple juice from pineapple fibers and starch from potatoes.

Figure 12:
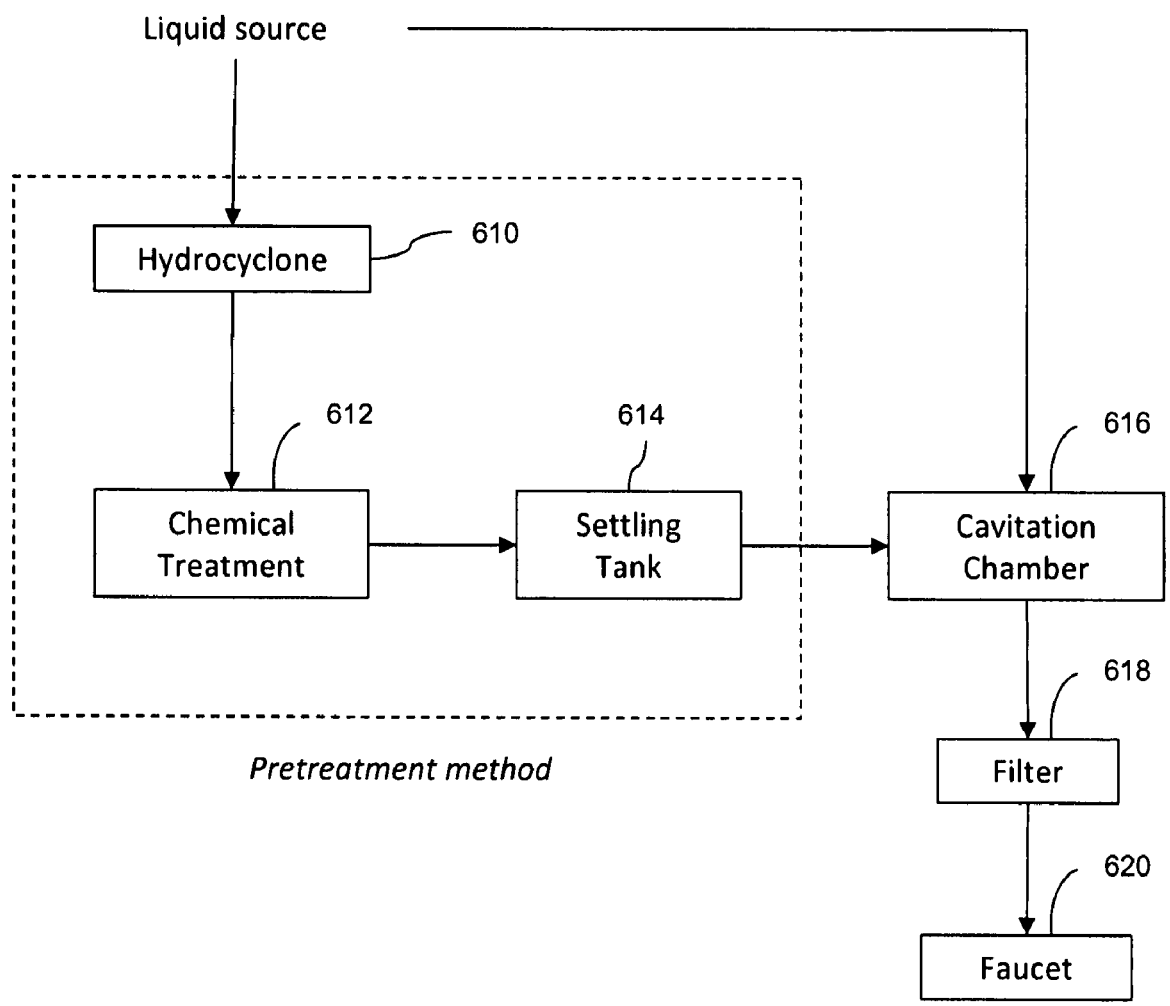
FIG. 12 is a flow diagram of a method of purification according to the present invention.

FIG. 12 shows a method for purifying liquid according to the present invention. If there are solids suspended in the liquid, the liquid preferably undergoes the pretreatment method of steps 610-614. If there are no solids suspended in the liquid, then the liquid may go directly to cavitation chamber 616. According to the pretreatment method, the liquid goes to a hydrocyclone 610 which helps to divide the liquid from the solids as discussed above in connection with the apparatus shown in FIG. 10. Next, the liquid undergoes chemical treatment 612, which preferably comprises adding coagulation chemicals which bond to sediment in the liquid and promote settling of the sediment. Settling tank 614 holds the liquid for an amount of time sufficient to allow the chemicals and sediment to settle at the bottom of the tank. The liquid in settling tank 614 then goes to cavitation chamber 616 where cavitation is induced within the liquid to kill undesirable organisms in the liquid. The undesirable organisms are killed by the rapid creation and implosion of the cavitation bubbles formed within the liquid. Cavitation chamber 616 may have a structure similar to any of the apparatuses 10, 110 and 210 described in connection with FIGS. 1-5. The cavitation may kill the organisms by cellular lysis. If the liquid to be purified is water, the cavitation and high temperature generated by the cavitation preferably promote ozonization of the water. The ozone kills undesirable organisms within the liquid. After undesirable organisms within the liquid are killed, the liquid is filtered at filter 618 removing any fine particulate remaining in the liquid before the liquid exits faucet 620.

Preferably, the cavitation chamber of the process shown in FIG. 12 has a structure like any of the apparatuses shown in FIGS. 1-5. Preferably, an apparatus used in the process of FIG. 12 has protrusions with a C-shaped top profile, as shown in FIG. 6, for maximizing cavitation within the liquid. An apparatus as shown in FIGS. 1-5 may be installed within a home or office to purify water entering the building from a public water line. Preferably, an apparatus installed for home or office water purification will have an inlet less than 0.5 inches and an outlet around 0.75 inches. An apparatus as shown in FIGS. 1-5 may also be installed within a water distribution line for purifying the water therein. The liquid that is purified using the method shown in FIG. 12 may be water, juice or any other liquid needing purification. For instance, this purification process may be used instead of or in addition to pasteurization to purify juice or milk. The purification process described herein is advantageous because the liquid is not heated and therefore the flavor of the liquid does not change. The purification process shown in FIG. 12 may also be used to purify wastewater.

The purification method of FIG. 12 may be used to purify liquid used for heat transfer. Undesirable organisms may flourish in water or other liquids used for heat transfer. It is desirable to kill these undesirable organisms to prevent sickness among individuals that may come into contact with the liquid. When liquid is used for heating purposes, a cavitation chamber and centrifuge may receive liquid from a heat exchanger, purify the liquid, then send the liquid to a boiler. The liquid then goes from the boiler to the heat exchanger and back to the cavitation chamber. When liquid is used for cooling purposes, a cavitation chamber may receive liquid from a heat exchanger, purify the liquid, then send the liquid to a cooling tower. The liquid then goes from the cooling tower to the heat exchanger and back to the cavitation chamber. The liquid purification may increase the efficiency of the heat transfer process by raising the specific heat capacity of the liquid.

Figure 13:
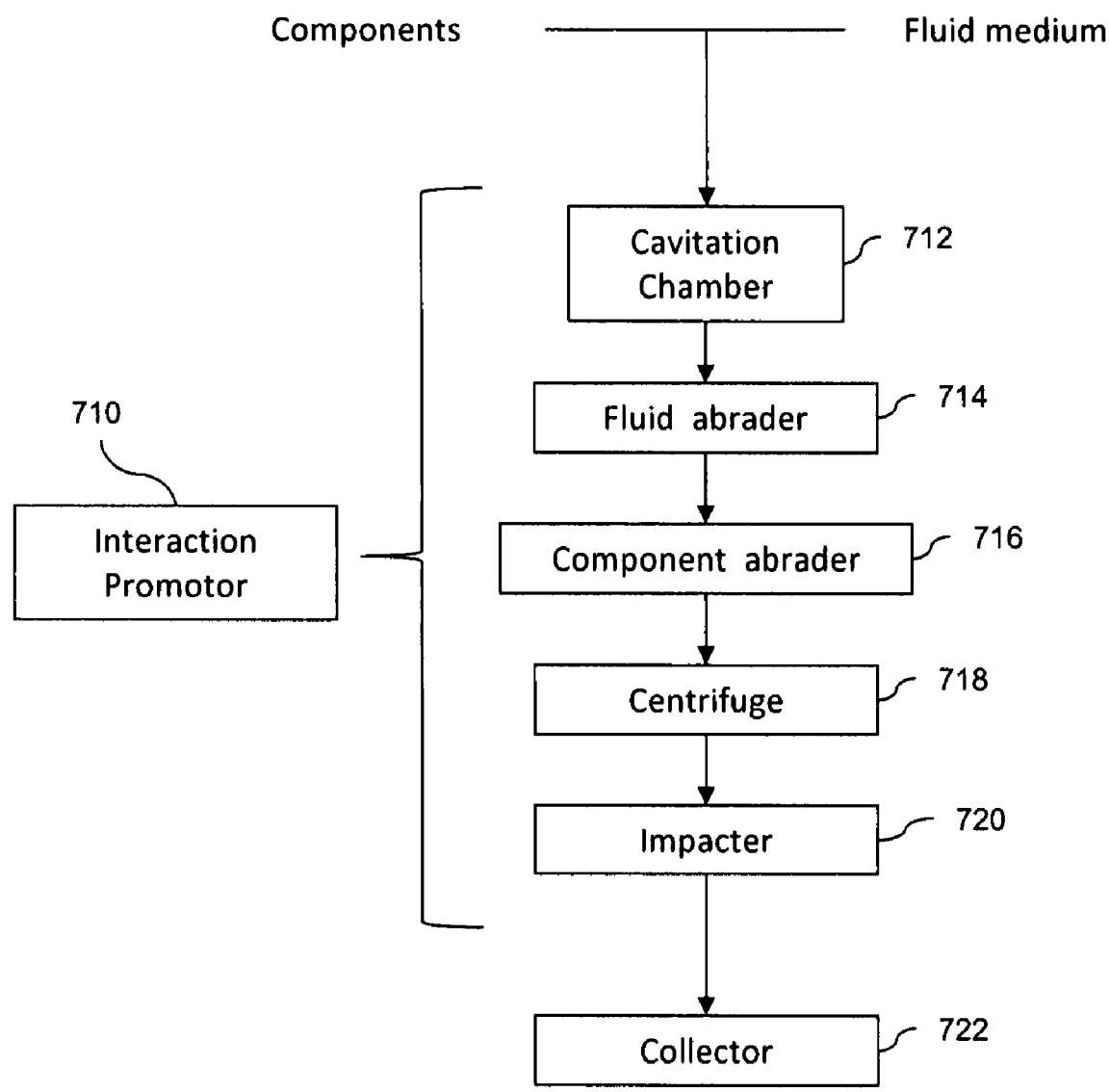
FIG. 13 is a flow diagram of a method of promoting interaction according to the present invention.

FIG. 13 shows a method of promoting interaction between two or more components in accordance with the present invention. The components are placed in a fluid medium and sent to an interaction promoter 710. Interaction promoter 710 has a cavitation chamber 712, a fluid abrader 714, a component abrader 716, a centrifuge 718 and an impactor 720. The interaction promoter may have a structure as any of the apparatuses 10, 110 and 210 described above in connection with FIGS. 1-5, and it should be appreciated that a single structure may simultaneously perform steps 712-720. Cavitation chamber 712 induces cavitation in the fluid for promoting interaction between the components. Fluid abrader 714 induces abrasion between the fluid and components and component abrader 716 induces abrasion between the components for promoting interaction between the components. Centrifuge 718 subjects the components to centrifugal force promoting interaction between the components, and impactor 720 subjects the components to an impact force to promote interaction between the components. Upon exiting interaction promoter 710, the interacted components are collected in a collector 722. The components which interact may be solid, liquid, gas, or any combination of the three.

The method of FIG. 13 may be used to promote any chemical or physical reaction, such as a hydrolysis reaction. For instance, the method may be used to promote the interaction of enzymes and starch for the purpose of hydrolyzing the starch. The starch and enzymes are placed in a fluid medium and sent through interaction promoter 710. The cavitation, abrasion, and other forces generated within the interaction promoter promote the interaction of the starch and enzymes resulting in the hydrolyzation of the starch. The method of FIG. 13 may further be used to promote saccharization of the hydrolyzed starch for creating a sugar syrup. The hydrolyzed starch and enzymes are placed in a fluid medium and sent through interaction promoter 710 which promotes the interaction of the enzymes and hydrolyzed starch. The cavitation, abrasion, and other forces generated within the interaction promoter promote the interaction of the hydrolyzed starch and enzymes to create a sugar syrup. The sugar syrup is then collected in collector 722.

The method of FIG. 13 may also be used for nixtamalizing corn. In a typical nixtamalization process corn is cooked in an alkali solution in order to separate the pericarp from the corn and dextrinize the starch in the corn endosperm. Nixtamalized corn is easier to grind into flour and the dextrinized starch is more nutritious. To nixtamalize corn according to the present method of promoting interaction, the corn is placed in an alkali solution preferably comprising calcium oxide and water. The corn and alkali solution are heated and then sent to interaction promoter 710 for promoting interaction between the corn and alkali solution. The corn is nixtamalized due to the combined effects of the forces generated within the interaction promoter which promote interaction with the alkali solution. The components of the corn may also be separated by the cavitation, abrasion and centrifugal and impact forces as discussed above with respect to the method of separating corn. After exiting interaction promoter 710, the corn goes to a dryer (not shown). Corn may be nixtamalized within about 5 minutes according to the method shown in FIG. 13. Using conventional methods, nixtamalization of corn takes about 12 hours.

It is also possible to emulsify, encapsulate and homogenize substances in accordance with the method for promoting interaction shown in FIG. 13. For example, the method may be used to produce banana puree from bananas, coconut crème from coconuts and meat broth from meat. The method may be used to emulsify fruit juices, ice cream, sauces, pharmaceutical pastes, chemical pastes and meat for sausage. The method may be used to promote the interaction of milk, fruit juices or fruit pulp with additional products before packaging. The method may also be used to accelerate a chemical or physical reaction occurring as a result of the interaction of two or more components. For instance, the method may be used to speed up the conversion of wood into pulp where the components for interaction comprise wood and one or more chemicals.

Figure 14:
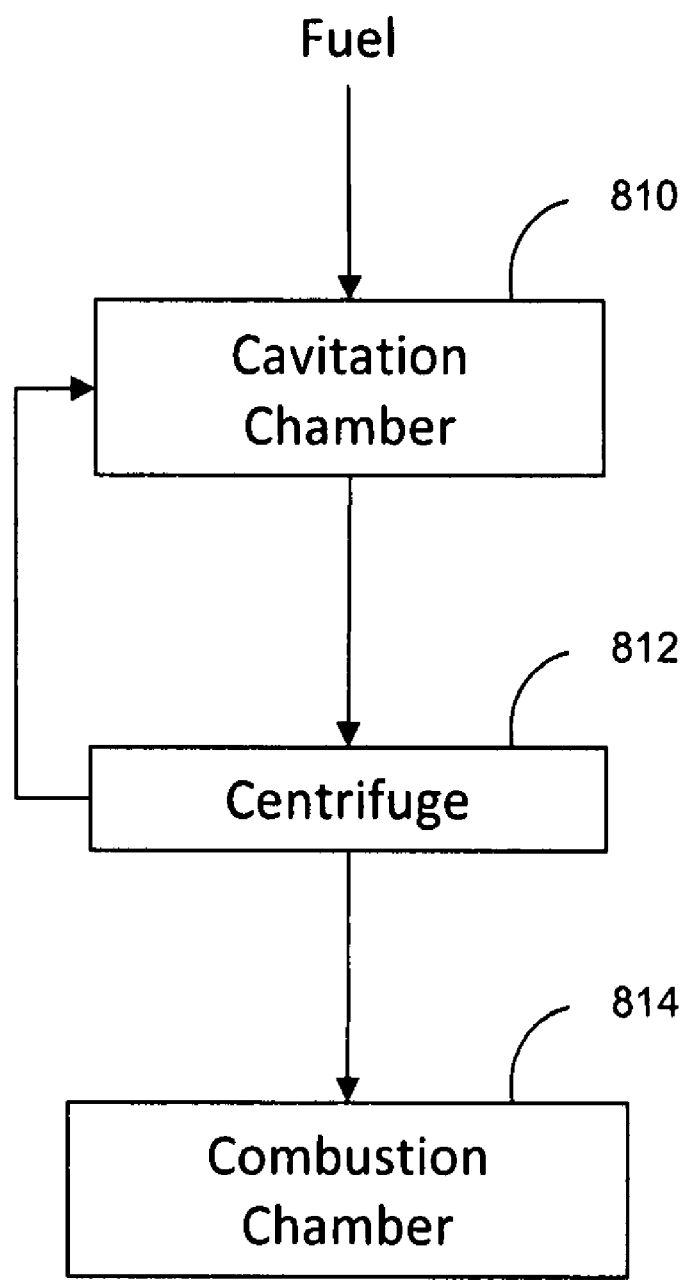
FIG. 14 is a flow diagram of a method of improving combustion according to the present invention.

FIG. 14 shows a method for improving the combustion of liquid fuel by vaporizing the liquid fuel. Vaporizing liquid fuel improves combustion because the fuel to air ratio is more evenly distributed throughout a combustion chamber 814. To vaporize fuel according to the present method, the fuel is sent through a cavitation chamber 810 where cavitation is induced in the fuel. The rapid creation and implosion of cavitation bubbles within the fuel vaporizes the fuel. After exiting the cavitation chamber 810 some liquid fuel may remain, therefore a centrifuge 812 subjects the vaporized and liquid fuel combination to centrifugal force dividing the vaporized fuel from the liquid fuel. Centrifuge 812 may have a similar structure as the hydrocyclone shown in FIG. 10. The vaporized fuel is mixed with oxygen and then combusted in a combustion chamber 814 and the liquid fuel is recycled back to cavitation chamber 810. Any apparatus shown in FIGS. 1-10 may be used to improve the combustion of liquid fuel according to the method shown in FIG. 14.

From the foregoing it will be seen that this invention is one well adapted to attain all ends and objectives herein-above set forth, together with the other advantages which are obvious and which are inherent to the invention.

Since many possible embodiments may be made of the invention without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. A method for separating the endosperm, pericarp, and germ of a plurality of corn kernels, said method comprising:
    placing the corn kernels in a fluid medium; and
    simultaneously inducing cavitation within the fluid and subjecting the corn kernels to centrifugal force to separate the endosperm, pericarp, and germ of the corn kernels wherein the kernels are not crushed by a mill or degerminator before separation separation.

2. The method of claim 1, further comprising inducing abrasion between the fluid and corn kernels to separate the endosperm, pericarp, and germ of the corn kernels.

3. The method of claim 1, further comprising inducing abrasion between the corn kernels to separate the endosperm, pericarp, and germ of the corn kernels.

4. The method of claim 1, further comprising subjecting the corn kernels to an impact force to separate the endosperm, pericarp, and germ of the corn kernels.

5. The method of claim 1, wherein the endosperm, pericarp, and germ of one of the corn kernels are separated in less than two minutes.

6. The method of claim 1, wherein the corn kernels are not steeped in water or an acidic solution before separation.

7. The method of claim 1, further comprising:
    dividing the germ and pericarp from the fluid and endosperm after separating the endosperm, germ, and pericarp;
    inducing cavitation within the fluid and endosperm to separate the starch and protein from the endosperm cells; and
    subjecting the separated starch and protein to centrifugal force to divide the starch and protein.

8. The method of claim 7, further comprising:
    hydrolyzing the starch;
    saccharizing the hydrolyzed starch to produce sugar syrup;
    fermenting the sugar syrup to produce liquid ethanol;
    inducing cavitation within the liquid ethanol to convert the liquid ethanol into ethanol vapor;
    subjecting the ethanol vapor to a centrifugal force to divide the ethanol vapor from the liquid; and
    condensing the ethanol vapor.

9. The method of claim 1, wherein the step of simultaneously inducing cavitation within the fluid and subjecting the corn kernels to centrifugal force is performed with a plurality of protrusions extending from a rotor, said protrusions being spaced no less than approximately 6 millimeters apart.

10. The method of claim 1, wherein the corn kernels are not crushed before the endosperm, pericarp, and germ are separated.

11. The method of claim 1, wherein the step of simultaneously inducing cavitation within the fluid and subjecting the corn kernels to centrifugal force is performed with an apparatus comprising:
    a housing presenting an interior chamber, an inlet adapted to allow the fluid and corn kernels to enter said chamber, a shaft opening, and an outlet adapted to allow the fluid and endosperm, pericarp, and germ to exit said chamber after the endosperm, pericarp, and germ are separated;
    a shaft projecting through said shaft opening into said chamber;
    a rotor coupled with said shaft inside of said chamber;
    a plurality of protrusions extending from said rotor, wherein said protrusions are spaced no less than approximately 6 millimeters apart; and
    a prime mover for rotating said shaft and rotor.

12. The method of claim 11, wherein the endosperm, pericarp, and germ are separated by the combined effects of centrifugal force, abrasion between the fluid and corn kernels, abrasion between the corn kernels, and impacts between the corn kernels and protrusions.

13. The method of claim 11, wherein said housing presents first and second end walls and a side wall defining said chamber, wherein said inlet is in said first end wall, said shaft opening is in said second end wall, and said outlet is in said side wall, and wherein said rotor presents a front surface facing said inlet and said plurality of protrusions extend from said front surface of said rotor toward said inlet.

14. The method of claim 13, wherein said rotor is circular and said protrusions are equidistant from the center of said rotor adjacent the peripheral edge of said front surface of said rotor, wherein said protrusions are cylindrical, and wherein there is an approximately 6 to 12 millimeter space between adjoining protrusions for retaining corn kernels within said chamber until separation of the germ, pericarp, and endosperm.

15. The method of claim 13, further comprising protrusions extending from said first end wall toward said rotor.

16. The method of claim 13, further comprising:
a tube received by said inlet and extending into said chamber;
a counter-rotor coupled with said tube inside of said chamber, said counter-rotor presenting a front surface facing said front surface of said rotor; and
protrusions extending from said front surface of said counter-rotor toward said rotor.

17. The method of claim 11, further comprising a centrifuge coupled to said outlet.

18. A method for separating joined components, said method comprising:
placing the joined components in a fluid medium; and
simultaneously inducing cavitation within the fluid and subjecting the joined components to centrifugal force to separate the joined components wherein the joined components are not crushed by a mill or degerminator before separation.

19. The method of claim 18, further comprising inducing abrasion between the fluid and joined components to separate the joined components.

20. The method of claim 18, further comprising inducing abrasion between the joined components to separate the joined components.

21. The method of claim 18, further comprising subjecting the joined components to an impact force to separate the joined components.

22. The method of claim 18, wherein the joined components are grains or beans.

23. The method of claim 22, wherein the joined components comprise the endosperm, germ, and pericarp of a corn kernel.

24. The method of claim 23, further comprising:
dividing the germ and pericarp from the fluid and endosperm after separating the endosperm, germ, and pericarp;
inducing cavitation within the fluid and endosperm to separate the starch and protein from the endosperm cells; and
subjecting the separated starch and protein to centrifugal force to divide the starch and protein.

25. The method of claim 24, further comprising:
hydrolyzing the starch;
saccharizing the hydrolyzed starch to produce sugar syrup;
fermenting the sugar syrup to produce liquid ethanol;
inducing cavitation within the liquid ethanol to convert the liquid ethanol into ethanol vapor;
subjecting the ethanol vapor to a centrifugal force to divide the ethanol vapor from the liquid; and
condensing the ethanol vapor.

26. The method of claim 18, wherein the joined components comprise the skin, pulp, mucilage, parchment, and beans of a coffee berry.

27. The method of claim 18, wherein the joined components comprise the skin, pulp, and pit of a fruit.

28. The method of claim 18, wherein the joined components comprise the starch and cells of a cassava root or potato.

* * * * *

UNITED STATES PATENT AND TRADEMARK OFFICE
CERTIFICATE OF CORRECTION

| | | |
|---|---|---|
| PATENT NO. | : 7,887,862 B2 | Page 1 of 1 |
| APPLICATION NO. | : 11/973692 | |
| DATED | : February 15, 2011 | |
| INVENTOR(S) | : Fernando Roberto Paz Briz and Fernando Roberto Paz Alcazar | |

It is certified that error appears in the above-identified patent and that said Letters Patent is hereby corrected as shown below:

Column 15,
Line 60, delete "separation separation." and insert -- separation. -- therefor.

Signed and Sealed this
Tenth Day of May, 2011

David J. Kappos
*Director of the United States Patent and Trademark Office*